United States Patent [19]

Thompson

[11] Patent Number: 4,872,457

[45] Date of Patent: Oct. 10, 1989

[54] APPARATUS FOR ASSISTED PARTURITION OF LIVESTOCK AND METHOD OF MAKING SAME

[76] Inventor: Howard D. Thompson, Rte. 4, Box 186, Brenham, Tex. 77833

[21] Appl. No.: 184,138

[22] Filed: Apr. 21, 1988

[51] Int. Cl.[4] .............................................. A61B 17/42

[52] U.S. Cl. .................................... 128/352; 294/191

[58] Field of Search ...................... 128/352, 361; 87/8, 87/9; 428/364, 369, 376, 398, 399; 24/115 H, 115 R; 254/1; 294/19.1, 74; 57/142; 119/1

[56] References Cited

U.S. PATENT DOCUMENTS 3,583,749 6/1971 Hopkins ............................... 294/74

FOREIGN PATENT DOCUMENTS 0145264 2/1931 Fed. Rep. of Germany ...... 128/352

0197120 4/1958 Fed. Rep. of Germany ...... 128/352

*Primary Examiner*—Michael H. Thaler
*Assistant Examiner*—William Lewis
*Attorney, Agent, or Firm*—David G. Henry

[57] ABSTRACT

An apparatus for use in assisted parturition of livestock. The apparatus comprises a single synthetic rope formed to have two small loops and one large loop. The small loops are adjustable when the loops are not under tension, and fixed when under tension. The small loops are for attachment to a fetus' forelimbs within its mother's uterus. The large loop remains outside of the birth canal and serve to transmit a traction force to the small loops for pulling the fetus through the birth canal. The fixed size of the small loops during use of the apparatus and the non-abrasive, synthetic rope reduces danger of injury to fetus and mother during assisted parturition.

11 Claims, 2 Drawing Sheets

APPARATUS FOR ASSISTED PARTURITION OF LIVESTOCK AND METHOD OF MAKING SAME

BACKGROUND OF THE INVENTION

1. Field of the Invention

Applicant's invention relates to the human assisted parturition of calves and other livestock offspring.

2. Background Information

While human interaction by way of selective breeding has produced larger, more disease-resistant, and generally more desirable specimens of domesticated livestock, such intervention has had the deleterious effect of rendering many species virtually incapable of non-assisted parturition.

A number of methods and apparatuses have been devised over the years for use in assisted parturition.

U.S. Pat. No. 1,326,800 issued to Spruyt discloses an apparatus including ropes which are tied at first ends to the legs of a calf and which are connected to a capstan at their other ends. A calf is then pulled through the birth canal as the ropes are pulled by turning the capstan.

U.S. Pat. No 1,604,714 issued to Nuesch discloses a combination of a lever having a hook eye on one end and a track with a plurality of pivotal points along its length for mating with the hook eye of the lever. The two longitudinal members of the track diverge at one end and are formed for resting against the upper thighs of a delivering cow. A rope member is attached to the four legs of the calf and to the lever at some midpoint along its length. The calf is pulled through the birth canal by pivoting the lever about successive pivotal points along the track, each time pulling the calf further through the birth canal.

U.S. Pat. No. 2,098,151 issued to Junge discloses a slip collar made of chain and attached to a longitudinal handle member. The end of the handle member having the slip collar attached thereto is inserted through the birth canal, the slip collar is positioned around a calf's forelegs and as the handle is pulled from the birth canal, the slip collar tightens around the forelegs permitting the user of the apparatus to pull the calf through the birth canal. The handle also includes an eye on the end opposite that of the slip collar which permits, by placing a rod through such eye and twisting, applying a torque to the calf and thereby rotating it along its axis for obtaining a more favorable position for parturition.

U.S. Pat. No. 2,668,539 issued to Dermody discloses an instrument for animal delivery including a flexible loop attached to one end of a flexible handle having a rigid cross member at its other end for ease of applying a traction force. The loop is simply placed around the fetus' neck and the fetus is pulled through the birth canal by applying a traction force to the cross member.

U.S. Pat. No. 2,709,438 discloses an adjustable obstetrical head snare which includes a bight of cable with a double-channeled sliding member associated with the juxtaposed cable leads thereof. The bight is placed over a fetus' head, a portion of the sliding member is positioned within the mouth of the fetus, and force is applied to the terminal ends of the cable to pull the fetus through the birth canal.

Each of the above-described apparatuses pose dangers to the fetus and/or to its mother or, in the alternative, are not particularly effective in achieving their stated objectives. In the case of the Spruyt invention, the use of slip knots or their equivalent at the ends of ropes poses a danger of crushing bones and surrounding tissues as the traction force is applied. The Neusch apparatus provides little more than an alternative source of traction force to be applied to that which is essentially a common rope attached to a fetus' forelimbs. The Junge apparatus poses a substantial danger to a fetus by virtue of lack of any control over the compressive force applied to the fetus' forelimbs resulting from the slip collar structure and by virtue of the use of chain with its propensity for crushing and abrading tissues to the detriment of the fetus and the mother.

The Dermody apparatus, includes a spring connected on one end to the loop which is placed over a fetus' head and on the other end with the cross member or handle. The spring is likely to pinch or cut the skin of the fetus or the interior surfaces of the mother's birth canal. Also, the loop placed around the head of the fetus is not adjustable and is, therefore, likely to slip from the fetus' head. The Murray apparatus poses similar dangers to those of the Junge apparatus in that there is no check on the compression exerted on the fetus and the use of cable presents hard and potentially injurious surfaces to the tissues of the fetus and of the mother.

It would, therefore, be desirable to provide a novel apparatus for assisting in the parturition of livestock, which apparatus permits a secure engagement with a fetus and is, therefore, effective in aiding in parturition. Further, it would be desirable to provide such an apparatus which would include means for checking the compressive force applied to a fetus and which would be made from materials lacking a tendency to injure the tissues of the fetus or its mother.

SUMMARY OF THE INVENTION

It is an object of the present invention to provide an apparatus for aiding in the parturition of livestock.

It is another object of the present invention to provide an apparatus for aiding in the parturition of livestock which apparatus facilitates effective engagement with the livestock fetus for pulling the fetus through the birth canal.

It is another object of the present invention to provide an apparatus for aiding in the parturition of livestock which apparatus includes means for checking the compressive force which is applied to the livestock fetus through use of such apparatus.

It is another object of the present invention to provide an apparatus for aiding in the parturition of livestock which apparatus by virtue of the materials from which is constructed lacks the propensity for injuring the livestock fetus or its mother through such apparatus' use.

In satisfaction of the above-stated objects, Applicant's present invention provides an apparatus for use in aiding parturition of livestock.

Applicant's invention is an apparatus constructed of synthetic rope in a manner which provides two small loops through which a livestock fetus' forelimbs are placed, an segment of rope intervening the two small loops, and a single larger loop. A traction force may be applied either to the segment intervening the small loops or to the large loop in pulling the fetus through the birth canal. The apparatus is constructed such that the small loops are adjustable in size and so force applied to the larger loop or the intervening segment serves only to draw the fetus through the birth canal and not to further reduce the size of the smaller loops resulting in possible injury to the fetus.

DETAILED DESCRIPTION OF THE PREFERRED EMBODIMENT

Figure 1:
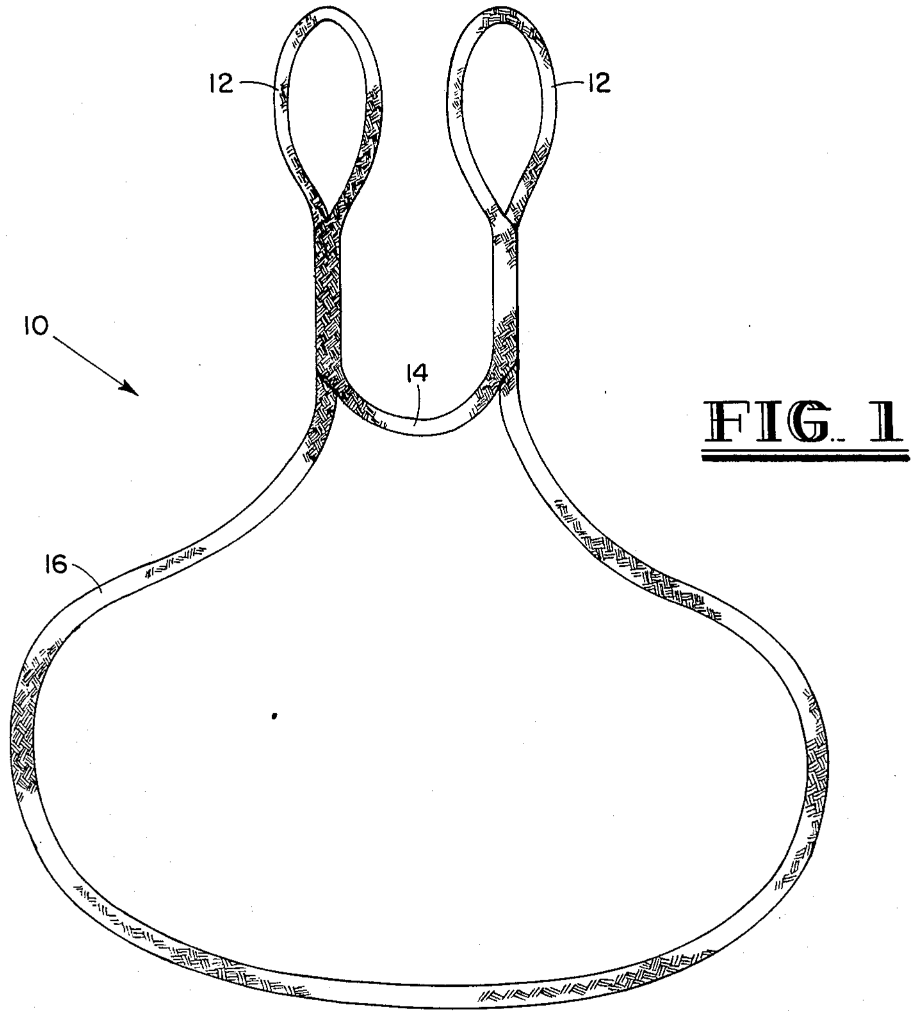
FIG. 1 is an elevational view of the preferred embodiment of Applicant's invention.

Referring to FIG. 1, the apparatus of Applicant's invention is referred to generally by the reference numeral 10. The apparatus 10 is formed from a single segment of synthetic rope approximately 14 feet in length. The apparatus 10 is formed to have two small loops 12, an interconnecting segment 14 and a large loop 16.

Figure 2:
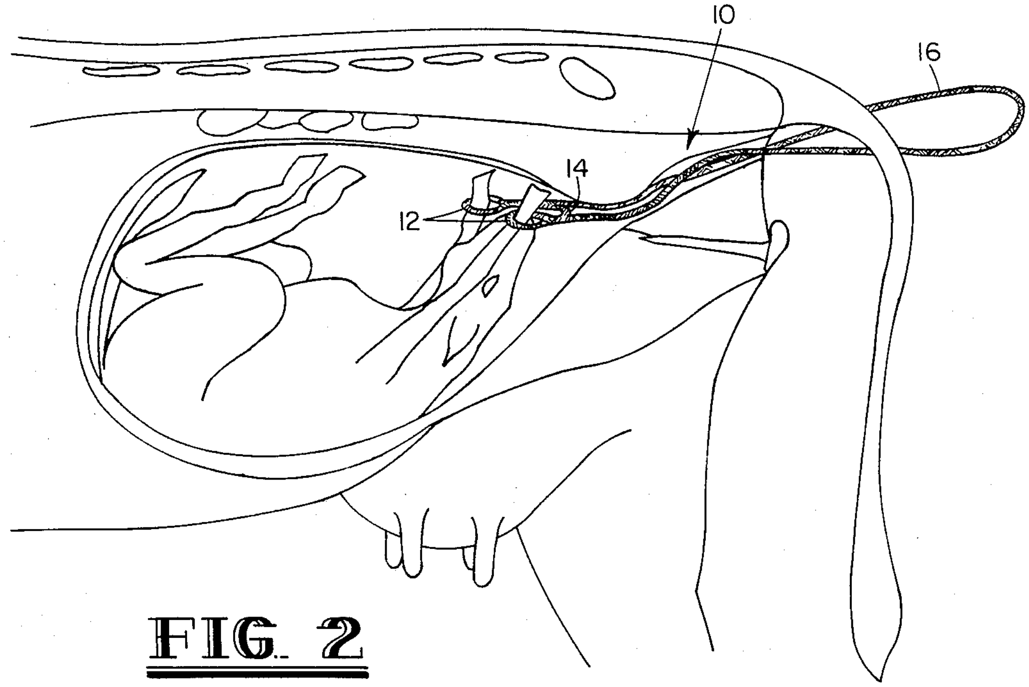
FIG. 2 is a sagittal cross-sectional view of Applicant's preferred embodiment in place for assisted parturition of a calf.

Referring to FIG. 2, when used for aided parturition of livestock, the end of the apparatus 10 having the two small loops 12 is inserted through the mother's birth canal and into the uterus. The small loops 12 are respectively placed on each of the fetus' forelimbs and are tightened snugly about the forelimbs. A traction force is applied to the portion of the apparatus 10 defining the large loop 16 and/or to the interconnecting segment 14 to pull the fetus through the birth canal. The apparatus 10 is constructed such that the traction force is translated only into movement of the fetus and not into contraction of the small loops 12.

The synthetic rope used to construct the apparatus 10 is woven so that longitudinal compression of any section thereof along the axis of the rope causes the constituent woven elements to separate such that a central, axiallyoriented channel is defined. A rope constructed in this manner is said to be "hollow woven." It is this construction which permits the apparatus 10 to be fashioned as hereinafter described.

Although variations in the particular positions of features of the apparatus 10 are possible without deleterious effect, the preferred arrangement and the least difficult manner to describe its construction are chosen for this discussion.

Figure 3:
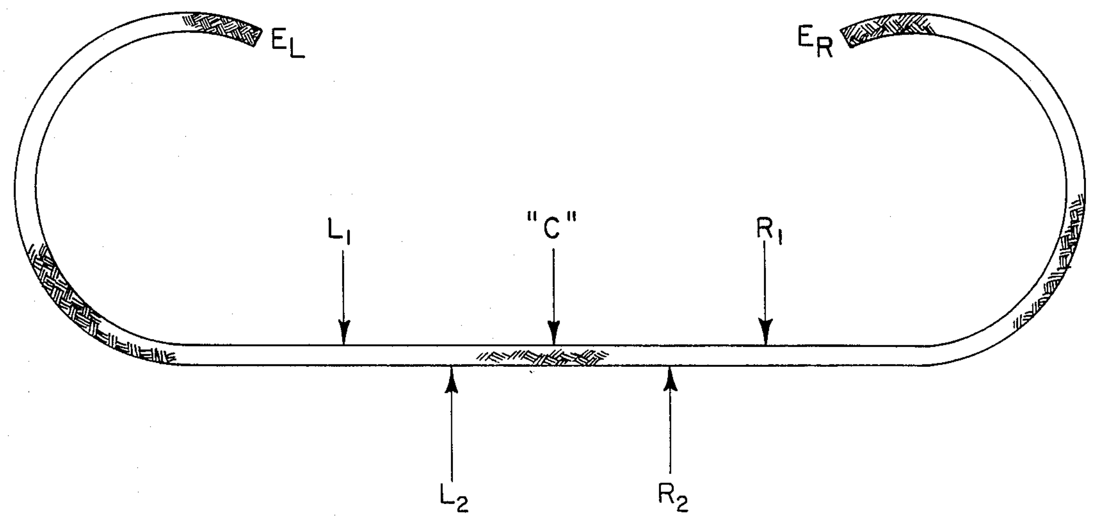
FIG. 3 is a view of a rope segment with reference points indicated thereon.
Figure 4:
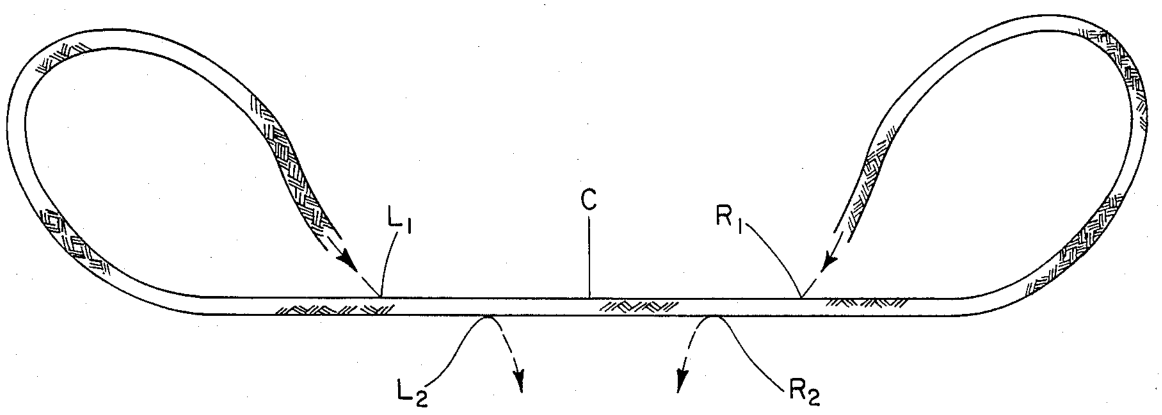
FIG. 4 is a view of a rope segment used in constructing the preferred embodiment of Applicant's invention with dashed lines indicating the path of the rope's ends taken in constructing the preferred embodiment.

Referring to FIGS. 3 and 4, a segment of hollow woven synthetic rope approximately 14 feet in length is required to make the apparatus 10. Five reference points should be marked on the rope. In the Figures, the reference points will be referred to as "C," the center point of the rope, or seven feet from either of the rope's ends; "$L_1$" a point nine inches to the left of "C;" "$L_2$," a point three inches to the left of "C;" "$R_1$," a point nine inches to the right of "C;" "$R_2$," a point three inches to the right of "C;"

The six inch segment of rope delineated by "$L_1$" and "$L_2$" is compressed to open the above-referenced central channel. A first aperture is opened in the constituent woven members of the rope at $L_1$ and the left end of the rope $E_L$ is inserted into the central channel at $L_1$. The rope is pushed through the channel over a distance of 6 inches, and then directed from the channel through a second aperture at $L_2$ to the outside of the rope. The left end $E_L$ is then pulled until a small loop is defined by the segment of the rope beginning and ending at $L_1$.

The six inch segment of rope delineated by "$R_1$" and "$R_2$" is compressed to open the above-referenced central channel. A third aperture is opened in the constituent woven members of the rope at $R_1$ and the right end of the rope $E_R$ is inserted into the central channel at $R_1$. The rope is pushed through the channel over a distance of 6 inches, and then directed from the channel through a fourth aperture at $R_2$ to the outside of the rope. The right end $E_R$ is then pulled until a small loop is defined by the segment of the rope beginning and ending at $R_1$.

After the two small loops 12 are formed by the just-described operations, the rope's ends "$E_L$" and "$E_R$" are braided or otherwise securely joined together to define the large loop 16 as shown in FIG. 1.

Passing one segment of hollow woven rope (the inner segment) through the central channel of another segment (the outer segment) results in a structure which may be called an adjustment arrester for purposes of applicant's invention. For each adjustment arrester, the sliding of the inner segment of rope relative to the outer segment is checked when a traction force is applied to the outer segment, but is substantially unencumbered when the outer segment is under no such force. A familiar example of this effect is found in the children's toy often known as the Chinese Handcuff. In that case, the child's fingers are analogous to the inner segment of the rope, while the "handcuff" is analogous to the outer segment.

In actual use of the apparatus 10, the resistance of the fetus to movement under a traction force applied to the large loop 16 serves as the force on the outer segments of the rope which causes the outer segments to check any further movement of the inner segments of the rope relevant to their respective outer segments. Therefore, once the small loops 12 are positioned on a fetus's forelimbs with the appropriate degree of snugness, the traction force used to pull the calf through the birth canal will not operate to further constrict the smaller loops and thereby risk injuring the fetus.

It is noted that applicants invention has utility aside from actual assistance in animal parturition. Commonly, calves or other animals are hung from their hind legs to drain amniotic fluid from the animal's respiratory tract. The apparatus 10 may be used in such operation with lesser tendency to injure the animal for the same reasons stated above with relation to assisted parturition. The apparatus 10 may likewise be used when hanging new born animals for weighing.

The nylon rope from which the apparatus 10 is constructed is preferable over potentially functionally equivalent members such as cables because a nylon rope has much less propensity for crushing or abrading the tissues of the fetus and/or its mother.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. An apparatus for assisted delivery of livestock comprising rope having a first segment, a second segment, a third segment, and a fourth segment:

said first segment being hollow woven and having a first axially oriented, central channel with a first aperture and a second aperture, said second aperture being displaced longitudinally on said rope from said first aperture;

said second segment being hollow woven and having a second axially oriented, central channel with a third aperture and a fourth aperture, said fourth aperture being displaced longitudinally on said from said third aperture, said second segment being displaced longitudinally on said rope from said first segment by said third segment which extends between said first segment at said second aperture and said second segment at said third aperture;

said fourth segment extending as a continuation of said first segment, forming a first loop and turning to enter said first channel at said first aperture, extending through said first channel, exiting said first channel at said second aperture, spanning between said first segment and said second segment, entering said second channel at said third aperture, extending through said second channel, exiting said second channel at said fourth aperture, extending past said fourth aperture forming a second loop and merging with the remainder of said rope as an extension of said second segment;

said first segment acting as a first adjustment arrester for arresting movement of said fourth segment inside said first channel when a traction force is applied to said first segment so said first loop is adjustable in size so long as no traction force is applied to said first segment, and is substantially fixed in size when a traction force is applied to said first segment;

said second segment acting as a second adjustment arrester for arresting movement of said fourth segment inside said second channel when a traction force is applied to said second segment so said second loop is adjustable in size so long as no traction force is applied to said second segment, and is substantially fixed in size when a traction force is applied to said second segment;

said first and second loops for placement about a livestock fetus' forelimbs for applying a traction force to said fetus, said loops when adjustable facilitating ease of engagement with said fetus and when fixed for safely applying said traction force without danger of crushing said forelimbs.

2. The invention of claim 1 wherein said apparatus is formed from a single piece of said rope, said single piece's ends being joined together after constructing said apparatus.

3. The invention of claim 2 wherein said rope is hollow woven synthetic rope.

4. The invention of claim 1 wherein said rope is hollow woven synthetic rope.

5. The invention of claim 1 wherein said first and said second segments are approximately six inches in length, said third segment is approximately one foot in length, and said fourth segment is approximately twelve feet in length.

6. An apparatus for assisted delivery of livestock comprising rope, said rope having a first end;

a second end;

a first axially oriented channel extending through a first portion of said rope from a first point on said rope less than half said rope's length from said first end to a second point further from said first end but less than half said rope's length from said first end;

a second axially oriented channel extending through a second portion of said rope from a third point on said rope less than half said rope's length from said second end to a fourth point further from said second end but less than half said rope's length from said second end;

a third portion of said rope delineated by said first end and said first point extending into said first channel at said first point and exiting said first channel to the outside of said rope at said second point;

a fourth portion of said rope delineated by said second end and said third point passing into said second channel at said third point end exiting said second channel to the outside of said rope at said fourth point;

said third portion of said rope defining a first loop including the intersection of said third portion with said first point;

said fourth portion of said rope defining a second loop including the intersection of said fourth portion with said second point;

said first and second ends being joined together on opposite sides of said first and second sections of said channels from said first and second loops to define a third loop;

said first loop and said second loop being adjustable when said first and second loops are not under tension, and fixed when said first and second loops are under tension.

7. The invention of claim 6 wherein said rope is hollow woven synthetic rope.

8. The invention of claim 7 wherein said first and said second portions of said rope are approximately six inches in length, said third portion is approximately six feet in length, and said fourth portion is approximately six feet in length.

9. The invention of claim 6 wherein said first and said second portions of said rope are approximately six inches in length, said third portion is approximately six feet in length, and said fourth portion is approximately six feet in length.

10. A method of making an apparatus for use in assisted delivery of livestock comprising the steps of:

selecting a piece of hollow woven rope having a central, axially oriented hollow channel;

selecting five reference points on said rope, including the midpoint of said rope's length, a first point nine inches in a first direction from said midpoint; a second point three inches in said first direction along said rope's length from said midpoint, a third point nine inches in a second direction on said rope from said midpoint, and a fourth point three inches in said second direction from said midpoint;

compressing a first six inch segment of rope delineated by said first point and said second point to open a first portion of said channel;

opening a first aperture in the constituent woven members of said rope at said first point;

inserting said rope's first end closest to said first point into said first portion of said channel at said first point;

pushing said first end through said first portion of said channel over a distance of 6 inches;

directing said first end from said channel through a second aperture at said second point to the outside of said rope;

compressing a second six inch segment of rope delineated by said third point and said fourth point to open a second portion of said channel;

opening a third aperture in the constituent woven members of said rope at said third point;

inserting said rope's second end closest to said third point into said second portion of said channel at said third point;

pushing said second end through said second portion of said channel over a distance of 6 inches; and directing said second end from said channel through a fourth aperture at said second point to the outside of said rope;

said first and second loops for placement about a livestock fetus' forelimbs for applying a traction force to said fetus, said loops when adjustable facilitating ease of engagement with said fetus and when fixed for safely applying said traction force without danger of crushing said forelimbs; and joining said first end with said second end.

11. A method of making an apparatus for use in assisted delivery of livestock comprising the steps of:

selecting a piece of hollow woven rope having a central, axially oriented hollow channel;

selecting five reference points on said rope, including the midpoint of said rope's length, a first point distanced from said midpoint in a first direction from said midpoint; a second point distanced from said midpoint in said first direction from said center point, but closer to said center point that said first point, a third point distanced from said midpoint in a second direction from said midpoint; and a fourth point distanced from said midpoint in said second direction from said center point, but closer to said center point than said third point;

compressing a first segment of said rope delineated by said first point and said second point to open a first portion of said channel;

opening a first aperture in the constituent woven members of said rope at said first point;

inserting said rope's first end closest to said first point into said first portion of said channel at said first point;

pushing said first end through said channel from said first point to said second point;

directing said first end from said channel through a second aperture at said second point to the outside of said rope;

compressing a second segment of said rope delineated by said third point and said fourth point to open a second portion of said channel;

opening a third aperture in the constituent woven members of said rope at said third point;

inserting said rope's second end closest to said third point into said second portion of said channel at said third point;

pushing said second end through the channel from said third point to said fourth point; and directing said second end from said channel through a fourth aperture at said second point to the outside of said rope;

said first and second loops for placement about a livestock fetus' forelimbs for applying a traction force to said fetus, said loops when adjustable facilitating ease of engagement with said fetus and when fixed for safely applying said traction force without danger of crushing said forelimbs; and joining said first end with said second end.

* * * * *